US009168080B2

(12) United States Patent
Wittenberger et al.

(10) Patent No.: US 9,168,080 B2
(45) Date of Patent: Oct. 27, 2015

(54) BALLOON CATHETER (75) Inventors: Dan Wittenberger, L'ile-Bizard (CA);
Claudia Lueckge, L'Île-Bizard (CA);
Réal Ste-Marie,
Notre-Dame-de-L'lle-Perrot (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 925 days.

(21) Appl. No.: 13/360,092

(22) Filed: Jan. 27, 2012

(65) Prior Publication Data
US 2013/0197497 A1  Aug. 1, 2013

(51) Int. Cl.
*A61B 18/02* (2006.01)
*A61B 18/14* (2006.01)
*A61B 18/00* (2006.01)

(52) U.S. Cl.
CPC .............. *A61B 18/02* (2013.01); *A61B 18/1492* (2013.01); *A61B 2018/0016* (2013.01); *A61B 2018/0022* (2013.01); *A61B 2018/0212* (2013.01); *A61B 2018/0262* (2013.01)

(58) Field of Classification Search
CPC ................... A61B 18/1492; A61B 2018/0016; A61B 18/1482; A61B 18/148; A61B 18/1485; A61B 19/201; A61B 2018/00214; A61B 2018/1467; A61B 2018/1475; A61B 2018/00011; A61B 2018/00178; A61B 2017/003; A61B 2018/1407; A61B 18/00; A61B 18/02; A61B 2018/0212; A61B 2018/0262; A61N 1/05
USPC .............................. 606/20–23, 25, 32, 34, 41
See application file for complete search history.

(56) References Cited

U.S. PATENT DOCUMENTS

| 5,617,854 | A | 4/1997 | Munsif |
| 5,673,695 | A | 10/1997 | McGee et al. |
| 6,622,731 | B2 * | 9/2003 | Daniel et al. ................. 128/898 |
| 7,837,676 | B2 | 11/2010 | Sinelnikov et al. |
| 2009/0138025 | A1 | 5/2009 | Stahler et al. |
| 2009/0287203 | A1 | 11/2009 | Mazzone et al. |
| 2009/0299355 | A1 | 12/2009 | Bencini et al. |
| 2010/0076402 | A1 | 3/2010 | Mazzone et al. |
| 2010/0204560 | A1 | 8/2010 | Salahieh et al. |
| 2011/0106074 | A1 | 5/2011 | Kunis et al. |

FOREIGN PATENT DOCUMENTS

| EP | 0573311 | A1 | 12/1993 |
| EP | 1384445 | A1 | 1/2004 |

OTHER PUBLICATIONS

CIPO,PCT/CA2012/001169. International Search Report, Feb. 18, 2013, pp. 1-7.
CIPO,PCT/CA2012/001169. Written Opinion, Feb. 18, 2013, pp. 1-6.

* cited by examiner

*Primary Examiner* — Deborah Malamud
(74) *Attorney, Agent, or Firm* — Christopher & Weisberg, P.A.

(57) ABSTRACT

A medical device including a catheter body defining a proximal portion and a distal portion. An expandable element is included defining a proximal end and a distal end, the proximal end being coupled to the distal portion of the catheter body. A tip element coupled to the distal end of the expandable element is included, the tip element including a shaft slideably receivable within a portion of the catheter body. A tensioning element coupled to the shaft and disposed within the expandable element is included, the tensioning element being engageable with the distal end of the catheter body and biasing the expandable element toward a pre-determined longitudinal position. An electrode array defining a substantially closed loop affixed to and extending from the tip element is also included.

10 Claims, 6 Drawing Sheets

BALLOON CATHETER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates cryogenic ablation devices, and more particularly, to an expandable membrane with an internally-fixed length compensator.

BACKGROUND OF THE INVENTION

Numerous procedures involving catheters and other minimally invasive devices may be performed to provide a wide variety of treatments, such as ablation, angioplasty, dilation or the like. Prior to insertion into a vessel and/or placement near a particular tissue region, the balloon is typically in a deflated state, and may include a number of folds that reduce the cross-sectional area of the balloon to ease insertion and/or placement. During a particular procedure, the balloon may be transitioned between inflated and deflated states in order to provide the desired effect. Such cycling can cause portions of the internal components of the catheter to experience axial movement as well as any distal tip portions. Moreover, when the balloon is deflated subsequent to a desired inflation, it may not necessarily deflate into its original, folded state occurring prior to use. Rather the balloon may bunch up or otherwise improperly deflate, causing the deflated balloon to have a larger than desirable radius, which may cause complications during the extraction and/or repositioning of the medical device.

In addition, when a balloon is employed, it often must be manufactured or constructed to have a particular shape or dimension for a specific application, and as such, any given catheter with a balloon may be limited to use in situations where the fixed dimensions of the balloon are appropriate. For example, a balloon may have a fixed radius in an inflated state, making it only suitable for a procedure requiring such a dimension or where a particular vasculature may accommodate that radius. As such, multiple catheters having varying fixed dimensions may be needed to successfully perform a desired treatment.

Accordingly, in light of the above limitations, it would be desirable to provide a medical device in which the balloon could be caused to deflate into its original, uninflated and folded orientation for ease of removal and/or repositioning. Moreover, it would be desirable to provide a medical device having an expandable element, such as a balloon, in which the particular size, shape, and/or dimensions of the balloon may be controlled and modified during use.

SUMMARY OF THE INVENTION

The present invention advantageously provides for a medical device including a catheter body defining a proximal portion and a distal portion. An expandable element is included defining a proximal end and a distal end, the proximal end being coupled to the distal portion of the catheter body. A tip element coupled to the distal end of the expandable element is included, the tip element including a shaft slideably receivable within a portion of the catheter body. A tensioning element coupled to the shaft and disposed within the expandable element is included, the tensioning element being engageable with the distal end of the catheter body and biasing the expandable element toward a pre-determined longitudinal position. An electrode array defining a substantially closed loop affixed to and extending from the tip element is also included.

In another embodiment, the medical device includes a catheter body defining a proximal portion and a distal portion. A fluid injection tube disposed within the catheter body and defining a plurality of fluid injection ports is included. An expandable element defining a proximal end and a distal end is included, the proximal end being coupled to the distal portion of the catheter body. A tip element coupled to the distal end of the expandable element is included, the tip element including a shaft slideably receivable within a portion of the catheter body, the shaft defining a plurality of fluid exhaust ports and in fluid communication with the catheter body. A spring coupled to the shaft and disposed within the expandable element is included, the spring being engageable with the distal end of the catheter body and biasing the expandable element toward a pre-determined longitudinal position. An electrode array defining a substantially closed loop affixed to and extending from the tip element is included.

In yet another embodiment, the medical device includes a catheter body defining a proximal portion and a distal portion. A fluid injection tube disposed within the catheter body is included, the fluid injection tube including a reservoir at its distal end, the reservoir defining a plurality of fluid injection ports. An expandable element defining a proximal end and a distal end is included, the proximal end being coupled to the distal portion of the catheter body. A tip element defining a proximal and distal end is included, the distal end of the tip element being coupled to the distal end of the expandable element, the tip element including a shaft slideably receivable within a portion of the catheter body, the shaft defining a plurality of fluid exhaust ports and in fluid communication with the catheter body. A spring coupled to the shaft and disposed within the expandable element is included, the spring being engageable with the distal end of the catheter body and biasing the expandable element toward a pre-determined longitudinal position. An electrode array defining a substantially closed loop affixed to and extending from the tip element is included, the substantially closed loop defining an adjustable internal diameter.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
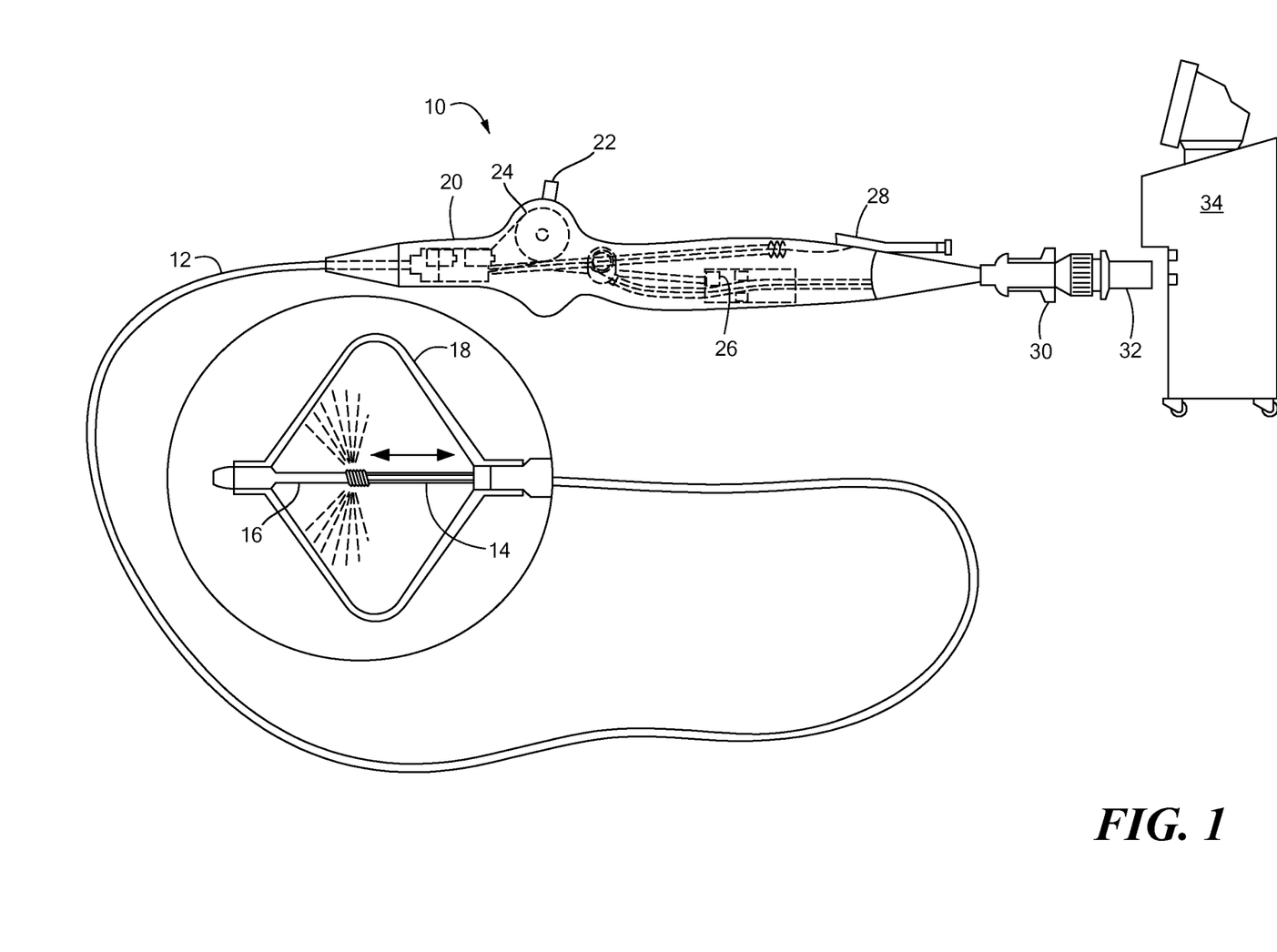
FIG. 1 illustrates an embodiment of a medical device in accordance with the present invention.
Figure 2:
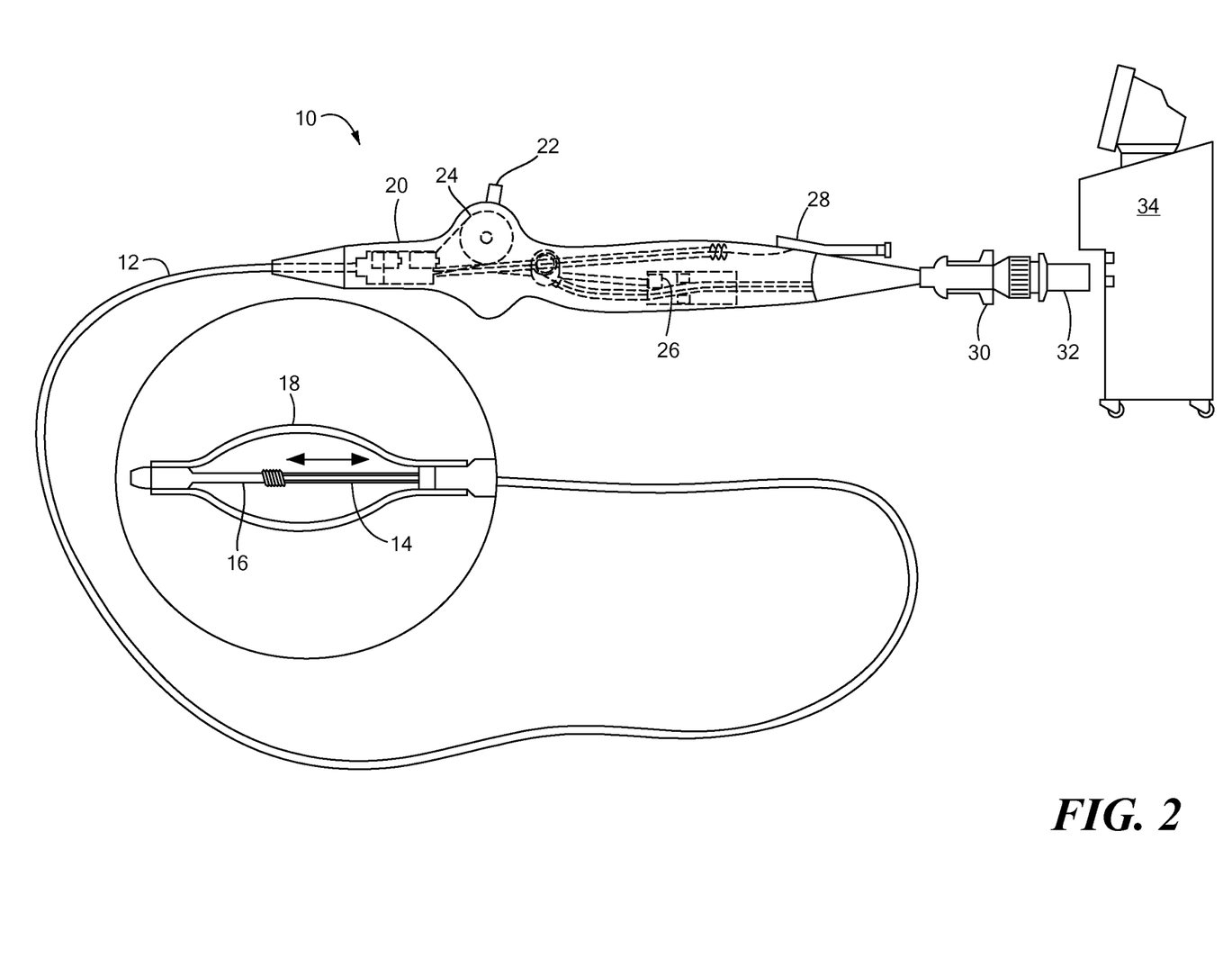
FIG. 2 shows an embodiment of a medical device in accordance with the present invention.

Now referring to the drawings in which like reference designators refer to like elements, there is shown in FIG. 1 an exemplary medical device and system constructed in accordance with the principles of the present invention, the medical device being designated generally as "10." Of note, the medical device 10 components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

The medical device 10 may include an elongate body 12, such as a catheter. The elongate body 12 may define a proximal portion and a distal portion, and may further include one or more lumens may disposed within the elongate body 12 thereby providing mechanical, electrical, and/or fluid communication between the proximal portion of the elongate body 12 and the distal portion of the elongate body 12. For example, the elongate body 12 may include an injection lumen 14 and an exhaust lumen defining a fluid flow path therethrough. In addition, the elongate body 12 may include a guidewire lumen 16 movably disposed within and/or extending along at least a portion of the length of the elongate body 12 for over-the-wire applications. The guidewire lumen 16 may define a proximal end and a distal end, and the guidewire lumen 16 may be movably disposed within the elongate body 12 such that the distal end of the guidewire lumen 16 extends beyond and out of the distal portion of the elongate body 12.

The medical device 10 of the present invention may further include an expandable element 18 at least partially disposed on the elongate catheter body. The expandable element 18 may include a balloon or other expandable structure, which may define a proximal end coupled to the distal portion of the elongate body 12 of the catheter, while further defining a distal end coupled to the distal end of the guidewire lumen 16. As such, due to the movable nature of the guidewire lumen 16 about the elongate body 12, any axial and/or longitudinal movement of the guidewire lumen 16 may act to tension or loosen the expandable element 18, i.e., extend or retract the expandable element 18 from a lengthened state to a shortened state during deflation or inflation, respectively. In addition, the expandable element 18 may have any of a myriad of shapes, and may further include one or more material layers providing for puncture resistance, radiopacity, or the like. The expandable element 18 may be in communication with the fluid injection and exhaust lumens of the medical device 10 as described above, i.e., a fluid flow path may provide an inflation fluid, such as a cryogenic fluid or the like, to the interior of the expandable element 18. In addition, a sheath (not shown) may be provided which is slidably positionable about at least a portion of the elongate body 12 of the medical device 10 and/or the expandable element 18.

The medical device 10 may include a handle element 20 coupled to the proximal portion of the elongate body 12, where the handle may include an element such as a lever or knob 22 for manipulating the catheter body and/or additional components of the medical device 10. For example, a pull wire with a proximal end and a distal end may have its distal end anchored to the elongate body 12 at or near the distal end. The proximal end of the pull wire may be anchored to an element such as a cam 24 in communication with and responsive to the lever. The handle 20 can further include circuitry for identification and/or use in controlling of the medical device 10 or another component of the system. For example, the handle may include one or more pressure sensors 26 to monitor the fluid pressure within the medical device 10. Additionally, the handle may be provided with a fitting 28 for receiving a guidewire that may be passed into the guidewire lumen 16, which may be partially disposed within the elongate body 12.

The handle may also include connectors that are matable directly to a fluid supply/exhaust and control unit or indirectly by way of one or more umbilicals for providing fluid communication with the elongate body 12. For example, the handle may be provided with a first connector 30 that is matable with a co-axial fluid umbilical (not shown) and a second connector 32 that is matable with an electrical umbilical (not shown) that can further include an accessory box (not shown). In an exemplary system, a fluid supply and exhaust, as well as various control mechanisms for the system may be housed in a single control unit 24. In addition to providing an exhaust function for the catheter fluid supply, the control unit 24 may also recover and/or re-circulate fluid delivered to the handle 20 and the elongate body 12 of the medical device 10. A vacuum pump in the control unit 34 may create a low-pressure environment in one or more conduits within the catheter body so that fluid is drawn into the conduit(s), away from the expandable element 18, and towards the proximal end of the catheter.

Figure 3:
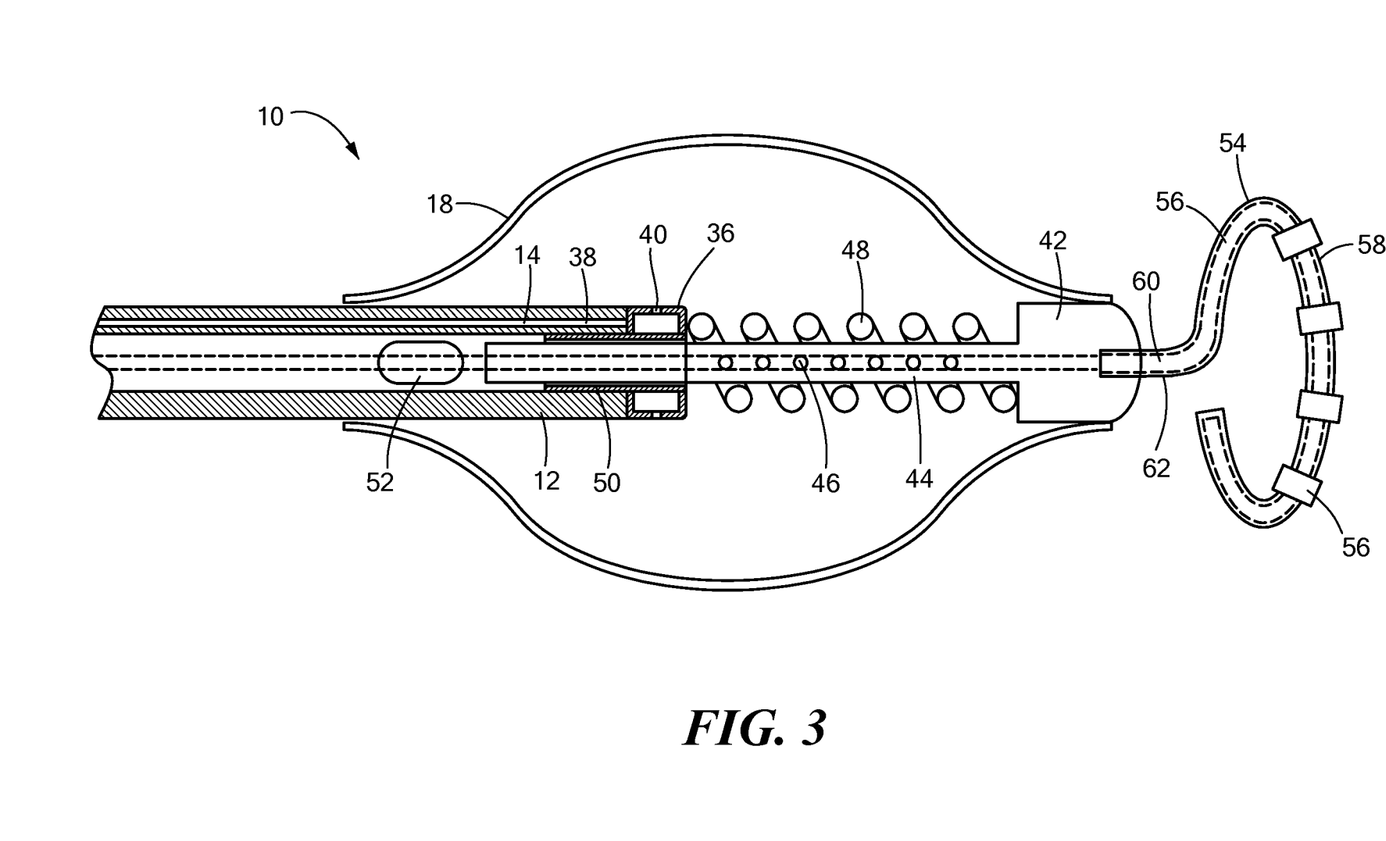
FIG. 3 is a side cross-sectional view of an embodiment of the present invention in which the tensioning element is disposed within an expandable element.

Now referring to FIG. 3, the medical device 10 may include the injection tube 14 extending into a portion of the interior of the expandable element 18. The fluid injection tube 14, as discussed above, may be in fluid communication a cryogenic fluid supply and may extend into a portion of the expandable element 18. The fluid injection tube 14 may be coupled to an interior portion of the elongate body 12 or surround the guidewire lumen 16 in over-the-wire-applications. Disposed at the distal end of the fluid injection tube 14 may be a fluid reservoir 36. The fluid reservoir 36 may be immovably affixed to the distal end of the fluid injection tube 14 to provide for a uniform spray distribution, or alternatively, may be movably affixed to the fluid injection tube 14. For example, the fluid reservoir 36 may be rotatable to provide for a particular spray distribution of cryogenic fluid. The fluid reservoir 36 may further be movably coupled to the fluid injection tube 14 by a connector 38 that may facilitate the axial movement of the fluid reservoir 36 along the interior of elongate body 12. The fluid reservoir 36 may further define a plurality of fluid injection ports 40 disposed on its exterior surface. The fluid injection ports 40 may be arranged in any pattern on the along surface of the fluid reservoir 36.

Continuing to refer to FIG. 3, affixed to the distal end of the expandable element 18 may be a tip element 42 defining a proximal and distal end. The distal end may be coupled to the distal end of the expandable element 18 such that a substantial portion of the tip element 42 may be substantially enclosed by the expandable element 18. The proximal end of the tip element 18 may also be coupled to a distal portion of the expandable element 18, such that the expandable element 18 is bonded along a substantial portion of the surface of the tip element 42. Alternatively, the distal end of the expandable element 18 may be coupled to the proximal end of the tip element 42, such that substantially the entire tip element 42 extends away from the distal end of the expandable element 18. The tip element 42 may be any shape or size, and in a particular embodiment, may be substantially rounded in shape such that the tip element 42 is atraumatic when contacting tissue to be treated.

Extending proximally from the tip element 18 toward the interior of the expandable element 18 may be a shaft 44. The shaft 44 may define a distal end coupled to the proximal end of the tip element 42 and a proximal end disposed and movable within a portion of the elongate body 12. The shaft 44 may be substantially cylindrical in shape, may be solid or hollow, and may define a diameter smaller than the diameter of the tip element 42. In particular, the shaft 44 may span at least the distance between the proximal end of the tip element 42 and the distal end of the elongate body 12. In an exemplary configuration, the shaft 44 defines an inner lumen in fluid communication with the interior of the expandable element 18 and with the elongate body 12. The shaft 44 may define a sufficient length such that the proximal end of the shaft 44 is disposed within the elongate body 12 at a distance proximal the fluid reservoir 36. In a particular configuration, the shaft 44 may define a plurality of fluid exhaust ports 46 along its major axis. The fluid exhaust ports 46 are operable to exhaust cryogenic fluid from the expandable element 18 into the elongate body 12 and to assist in the deflation of the expandable element 18. In an exemplary embodiment, the fluid exhaust ports 46 are axially disposed along the major axis of the shaft 44.

Continuing to refer to FIG. 3, the medical device 10 may include a tensioning element 48 disposed within the expandable element 18 for both non-over-the-wire applications as well as over-the-wire-applications. The tensioning element 48 provides tension to the expandable element 18 for automatic length compensation of the expandable element 18 for proper inflation and deflation of the expandable element 18. The tensioning element 48 may be composed of, for example, shape memory material such as nitinol or stainless steel. In an exemplary configuration, the tensioning element 48 is a coiled spring, but alternatively may be flexible tube or a plurality of flexible wires as discussed in more detail below. The tensioning element 48 may be disposed around a portion of the shaft 44 to bias the expandable element 18 toward a pre-determined longitudinal position. For example, the tensioning element 48 may be a spring radially disposed around the shaft 44. The tensioning element 48 may span the distance between the proximal end of the tip element 42 and the distal end of the elongate body 12. In an exemplary operation, when the tensioning element 48 is in its relaxed state, it longitudinally biases the expandable element 18 in a pre-determined position. The biased pre-determined position of the expandable element 18 may facilitate the proper deflation and pre-inflation state of the expandable element 18.

Figure 4:
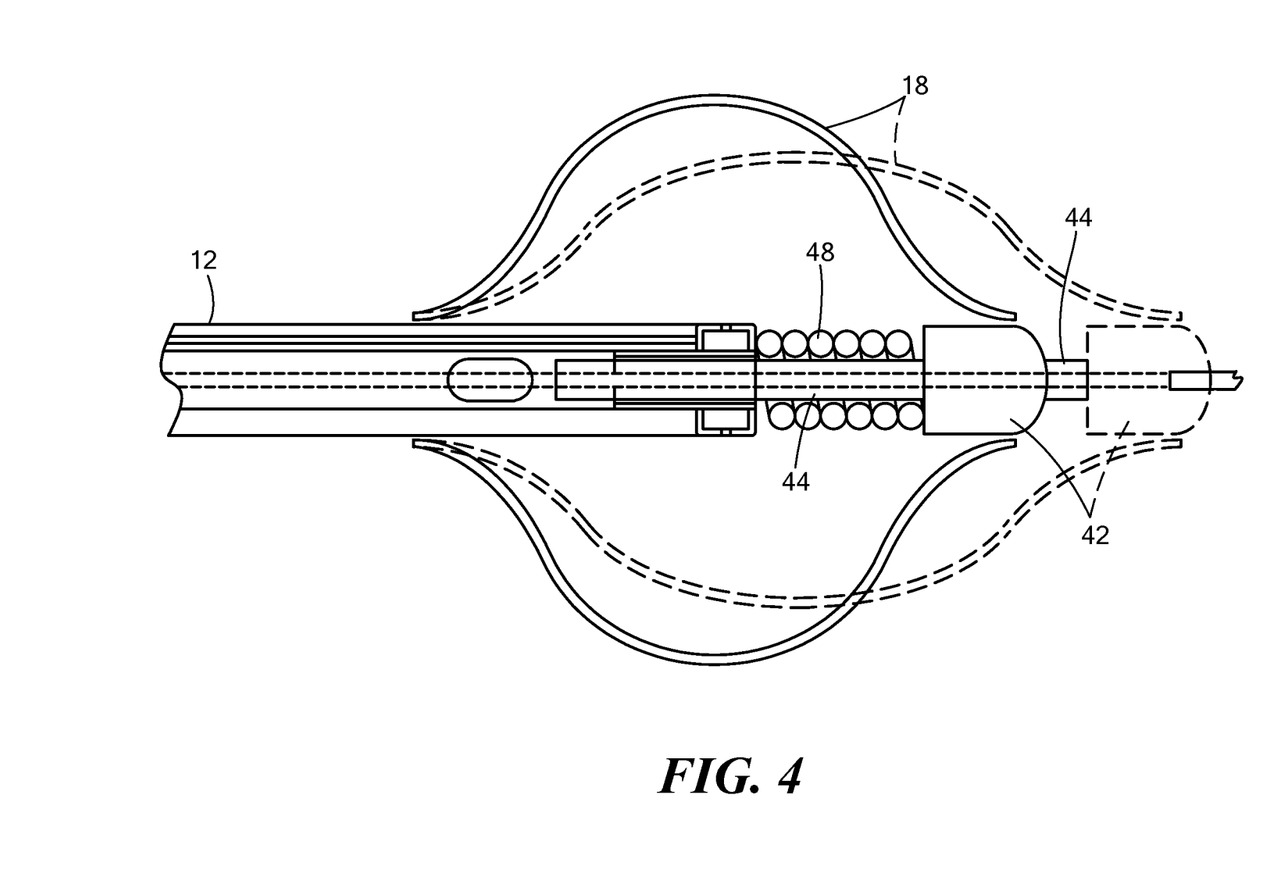
FIG. 4 is a side cross-sectional view of the embodiment shown in FIG. 3 showing the movement of the expandable element during inflation and deflation.

For example, as shown in FIG. 4, the bias from the tensioning element 48 may stretch the expandable element 18 such that it defines a substantially low-profile for insertion and removal from the vasculature, as illustrated by the broken lines. When the expandable element 18 inflates, as indicated by the solid line of the expandable element 18, the tip element 42 flexes and is pulled proximally toward the elongate body 12 and applies pressure to the tensioning element 48. The tensioning element 48 facilitates a predictable inflation shape and size of the expandable element 18. Further, in a configuration in which the tensioning element 48 is composed of nitinol, as the temperature within the expandable element 18 decreases, the tensioning element 48 becomes less elastic, which facilitates the expansion of the expandable element 18. When the temperature within the expandable element 18 increases as cryogenic fluid is evacuated, the tensioning element 48 may regain its elasticity to bias the expandable element 18 for proper deflation.

Referring back now to FIG. 3, to facilitate the longitudinal movement of the shaft 44 within the elongate body 12, a guide element 50 may be included coupled to the interior of the elongate body 12 proximate the distal end of the elongate body 12. The guide element 50 may be a tube or other structure that contacts the exterior surface of the shaft 44 as it moves within the elongate body 12. The guide element 50 facilitates the longitudinal movement of the shaft 44 within the elongate body such that there is a smooth and axial movement of the shaft 44 during inflation and deflation of the expandable element 18. Positioned proximal the distal end of the shaft 44 and the proximal end of the guide element 50 may be a second fluid exhaust port 52 defined by the elongate body 12. The second fluid exhaust port 52 operates to exhaust cryogenic fluid exhausted through the exhaust ports 46 out of the shaft 44 and into a fluid exhaust lumen.

Movably or immovably affixed to the distal end of the tip element 42 may be an electrode array 54. The electrode array 54 may include a plurality of electrodes 56 for measuring electrical activity of the target tissue region to be treated. The electrodes 56 may be disposed adjacent one another within or on the surface of the electrode array 54 to measure impedance and/or other forms of electrical activity to map the target tissue region. The electrode array 54 may include a shape memory alloy actuator wires 56 disposed within the electrode array 54 and in electrical communication with a power source. In particular, the electrode array 54 may include, several nickel-titanium wires 56 that contract or flex (typically 2%-10% of their length) like muscles when electrically driven or heated. The actuator wires 56 may extend through the entirety electrode array 54, the shaft 44, and through the elongate body 12 to be in electrical communication with a power source. Alternatively, the actuator wires 56 may extend through a substantially looped portion 58 of the electrode array 54 and be electrically connected to non-actuating conductive wires 60 disposed within a substantially longitudinal portion 62 of the electrode array 54.

In particular, the electrode array 54 may have at least two configurations. In a first configuration, the actuator wires 56 may be disposed within both the substantially looped portion 58 and the substantially longitudinal portion 62, the actuator wires 56 being in communication with a power source. In this first configuration, when an electric current is applied to the electrode array 54, both the length of the substantially longitudinal portion 62 and the diameter of the substantially looped portion 58 may be adjusted to provide for a particular configuration to map the tissue to be treated. The application of current may cause the simultaneous extension of the substantially longitudinal portion 62 and the increase in diameter of the substantially looped portion 58. Further, because the tip element 42 is fixed to the distal end of the expandable element 18, the electrode array 54 may be independently adjustable during the inflation and deflation of the expandable element 18. Thus, the electrical mapping of tissue adjacent the expandable element 18 may be achieved accurately whether the expandable element 18 is inflated or deflated, as the inflation and deflation of the expandable element 18 does not interfere with the adjustment of the electrode array 54.

In a second configuration, only the substantially looped portion 58 includes the actuator wires 56, and the substantially longitudinal portion 62 includes non-actuating wires 60. Thus, when current is applied to the electrode array 54, the length of the substantially longitudinal portion 62 remains constant while the diameter of substantially looped portion 58 increases. The second configuration may be utilized, for example, when the electrode array 54 is in contact with a target tissue, for example, when the substantially looped portion 58 substantially surrounds the pulmonary vein. In such a position, the surgeon may desire to adjust the diameter of the electrode array 54 without modifying its longitudinal position.

Figure 5:
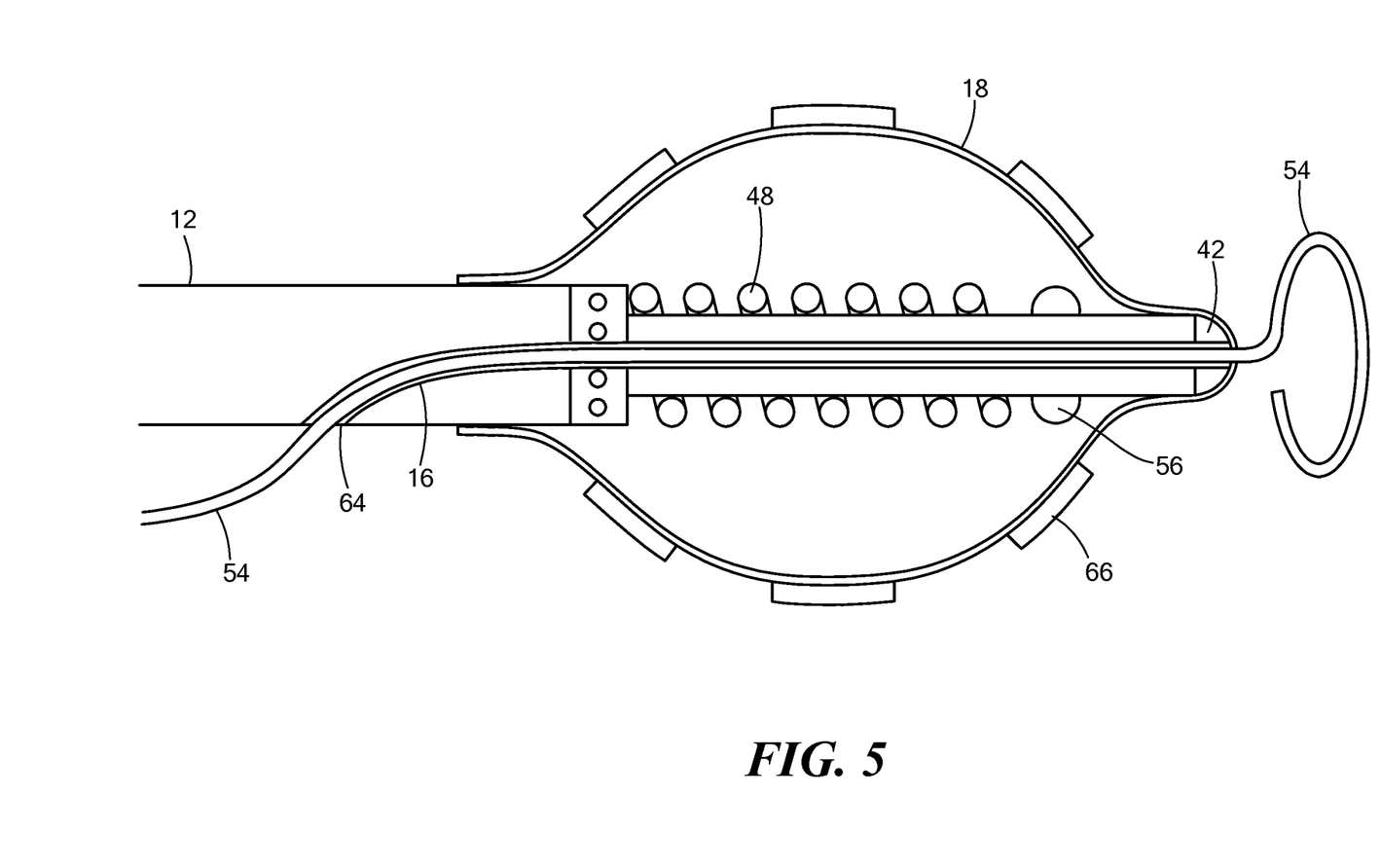
FIG. 5 is a side cross-sectional view of another embodiment of the present invention shown in FIG. 3 defining a rapid exchange port for over-the-wire applications.

Now referring to FIG. 5, in another configuration with the tensioning element 48 being disposed within the expandable element 18, the elongate body 12 may include the guidewire lumen 16 for over-the-wire applications. In particular, the elongate body 12 may include the guidewire lumen 16 extending from its proximal end through the distal end of the tip element 42. In such a configuration, the electrode array 54 may be removably inserted within the guidewire lumen 16 and advanced toward and out the distal end of the distal end of the tip element 42. The tip element 42 may further define an aperture or lumen to facilitate the insertion of the electrode array 54 out through its distal end. In particular, the electrode array 54 may be in a substantially linear configuration when inserted into the elongate body 12 and out through the distal end of the tip element 42. A low level electric current may then be applied to the electrode array to cause its distal end having the actuator wires 56 to flex can define the substantially looped portion 58. Optionally, a rapid exchange port 64 may be defined toward the distal end of the elongate body 12. The electrode array 54 and/or other medical devices may be removably inserted through the rapid exchange port 64 to perform any number of desired medical procedures.

Alternatively, one or more conductive strips 66 may be coupled to the surface of the expandable element 18. The conductive strips 66 may be in communication with a power supply and may operate to map the tissue region when the expandable element 18 is inflated. The conductive strips 66 may be in communication with the same power source as the electrode array 54 via the wires 60 and may define any shape or size to facilitate a desired mapping of the target tissue region.

Figure 6:
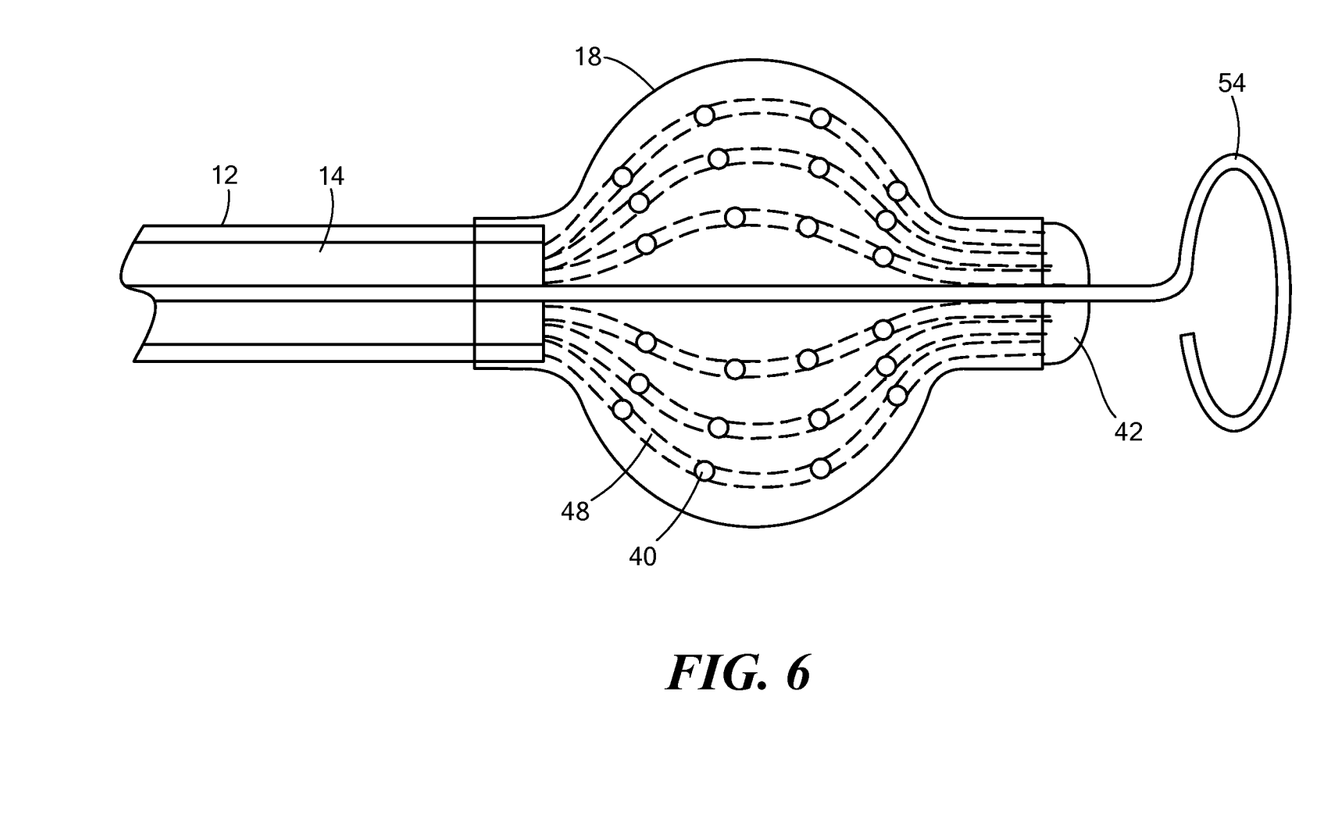
FIG. 6 is a side cross-sectional view of another embodiment of the present invention in which the tensioning element is disposed within an expandable element.

Now referring to FIG. 6, in another configuration, the tensioning element 48 may be a plurality of tubular or solid struts disposed within the expandable element 18 and spanning the space between the distal end of the elongate body 12 and the tip element 42. The tensioning element 48 may contour the expandable element 18 or alternatively may be spaced a distance from the interior wall of the expandable element 18. In an exemplary operation, the struts 48 are fused or otherwise affixed to the distal end of the elongate body 12 and within the interior of the tip element 42. As the expandable element 18 is inflated the struts 48 become less elastic and facilitate the inflation of the expandable element 18 in a controlled manner. As the expandable element 18 is deflated, the struts 48 bias the tip element 42 toward a distal position to facilitate deflation of the expandable element 18. Optionally, the struts 48 may be in fluid communication with the fluid injection tube 14 and further define the plurality of fluid injection ports 40 along the span between the distal end of the elongate body 12 and the tip element 42. In such a configuration, fluid may be dispersed and/or exhausted from the ports 42 such that uniform injection and exhaustion of the expandable element may be commensurate with the expansion and deflation of the expandable element 18.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    a catheter body defining a proximal portion, a distal portion, and a longitudinal axis;
    an expandable element defining a proximal end and a distal end, the proximal end being coupled to the distal portion of the catheter body;
    a tip element including a distal portion that is affixed to the distal end of the expandable element and being at least partially disposed within the expandable element, the tip element further including a shaft that extends proximally from the distal portion of the tip element and that is slideably receivable within a portion of the catheter body;
    a tensioning element coupled to the shaft and disposed within the expandable element, the tensioning element being engageable with the distal end of the catheter body and biasing the expandable element toward a pre-determined longitudinal position along the longitudinal axis; and
    an electrode array defining a substantially closed loop affixed to and extending from the tip element.

2. The medical device of claim 1, further comprising a fluid injection tube at least partially disposed within the expandable element, the fluid injection tube defining proximal and distal end, the fluid injection tube including a reservoir at its distal end, the reservoir being disposed within the expandable element.

3. The medical device of claim 2, wherein the reservoir defines a plurality of fluid injection ports.

4. The medical device of claim 1, wherein the shaft defines a plurality of fluid recovery ports between the proximal end of the tip element and the distal end of the catheter body.

5. The medical device of claim 1, wherein the substantially closed loop of the electrode array defines an inner diameter, and wherein the inner diameter is adjustable by application of current to the electrode array.

6. The medical device of claim 1, further comprising at least one conductive wire in electrical communication with the electrode array, the wire being disposed within a portion of the shaft and the catheter body.

7. The medical device of claim 1, wherein the tensioning element is a spring surrounding the shaft.

8. The medical device of claim 1, wherein the catheter body defines a port sized to receive a guidewire.

9. The medical device of claim 1, further comprising a plurality of electrodes coupled to the exterior surface of the expandable element.

10. The medical device of claim 1, wherein the catheter body defines a fluid return port proximal the shaft.

* * * * *